(12) United States Patent
Kalita et al.

(10) Patent No.: US 11,577,960 B2
(45) Date of Patent: Feb. 14, 2023

(54) METHOD OF FORMING A GRAPHENE DEVICE USING POLYMER MATERIAL AS A SUPPORT FOR A GRAPHENE FILM

(71) Applicants: Centre National de la Recherche Scientifique, Paris (FR); UNIVERSITE GRENOBLE ALPES, Saint Martin d'Heres (FR)

(72) Inventors: Dipankar Kalita, Grenoble (FR); Vincent Bouchiat, Biviers (FR); Laetitia Marty, Quaix en Chartreuse (FR); Nedjma Bendiab, Grenoble (FR)

(73) Assignees: Centre National de la Recherche Scientifique, Paris (FR); UNIVERSITE GRENOBLE ALPES, Grenoble (FR)

( * ) Notice: Subject to any disclaimer, the term of this patent is extended or adjusted under 35 U.S.C. 154(b) by 0 days.

(21) Appl. No.: 15/557,039

(22) PCT Filed: Mar. 9, 2016

(86) PCT No.: PCT/EP2016/054963
§ 371 (c)(1),
(2) Date: Sep. 8, 2017

(87) PCT Pub. No.: WO2016/142400
PCT Pub. Date: Sep. 15, 2016

(65) Prior Publication Data
US 2018/0057361 A1    Mar. 1, 2018

(30) Foreign Application Priority Data

Mar. 9, 2015 (FR) ...................................... 1551931

(51) Int. Cl.
*C01B 32/186* (2017.01)
*G06F 3/01* (2006.01)
(Continued)

(52) U.S. Cl.
CPC ............ *C01B 32/186* (2017.08); *B32B 27/12* (2013.01); *C01B 32/194* (2017.08); *G06F 3/014* (2013.01);
(Continued)

(58) Field of Classification Search
CPC ..... C01B 32/186; C01B 32/194; B32B 27/12; B32B 2313/04; G06F 3/0426; G06F 3/014
See application file for complete search history.

(56) References Cited

U.S. PATENT DOCUMENTS 7,945,302 B2    5/2011  McAdams
9,567,223 B2    2/2017  Song et al.
(Continued)

FOREIGN PATENT DOCUMENTS

CN    101048055          10/2007
CN    102920452 A    *   2/2013
(Continued)

OTHER PUBLICATIONS

Jung et al., KR 10-2014-0015927,Translation (Year: 2014).*
(Continued)

*Primary Examiner* — David D Davis
(74) *Attorney, Agent, or Firm* — Kaplan Breyer Schwarz, LLP

(57) ABSTRACT

The invention concerns a method of forming a graphene device, the method comprising: forming a graphene film (100) over a substrate; depositing, by gas phase deposition, a polymer material covering a surface of the graphene film (100); and removing the substrate from the graphene film (100), wherein the polymer material forms a support (102) for the graphene film (100).

4 Claims, 3 Drawing Sheets

(51) Int. Cl.
  C01B 32/194   (2017.01)
  B32B 27/12    (2006.01)
  G06F 3/042    (2006.01)
(52) U.S. Cl.
  CPC ........ *G06F 3/0426* (2013.01); *B32B 2313/04* (2013.01)

(56) References Cited

U.S. PATENT DOCUMENTS

| | | | |
|---|---|---|---|
| 10,164,220 B1* | 12/2018 | Lim | H01M 50/133 |
| 2012/0103670 A1* | 5/2012 | Lettow | B82Y 30/00 |
| | | | 174/258 |
| 2012/0282419 A1 | 11/2012 | Ahn et al. | |
| 2013/0090542 A1 | 4/2013 | Kipke et al. | |
| 2013/0130037 A1* | 5/2013 | Bol | H01L 51/0048 |
| | | | 428/408 |
| 2013/0285970 A1* | 10/2013 | Ahn | G06F 3/044 |
| | | | 345/173 |
| 2014/0010744 A1 | 1/2014 | Ruona et al. | |
| 2014/0145139 A1 | 5/2014 | Huang et al. | |
| 2014/0326700 A1 | 11/2014 | Bouchiat et al. | |
| 2014/0336597 A1 | 11/2014 | Coulthard et al. | |
| 2015/0098891 A1 | 4/2015 | Song et al. | |
| 2015/0343202 A1* | 12/2015 | Picaud | A61N 1/0526 |
| | | | 607/116 |
| 2016/0169754 A1* | 6/2016 | Kowalewski | G01L 5/228 |
| | | | 73/862.046 |
| 2017/0057827 A1 | 3/2017 | Sultana et al. | |
| 2018/0056057 A1 | 3/2018 | Kalita et al. | |

FOREIGN PATENT DOCUMENTS

| | | | | |
|---|---|---|---|---|
| CN | 102925859 | | 2/2013 | |
| CN | 104000624 | A | 8/2014 | |
| CN | 102920452 | B | 2/2015 | |
| EP | 2747158 | A1 * | 6/2014 | A61N 1/05 |
| EP | 2747158 | A1 | 6/2014 | |
| EP | 2778757 | A1 | 9/2014 | |
| JP | 2011-051801 | A | 3/2011 | |
| KR | 20140015927 | A | 2/2014 | |
| TW | M487718 | U | 10/2014 | |
| WO | 2013/116675 | A1 | 8/2013 | |
| WO | 2014/145139 | | 9/2014 | |
| WO | 2015020610 | A1 | 2/2015 | |

OTHER PUBLICATIONS

Authorized Officer: Follens, Lana, "International Search Report and Written Opinion" issued in counterpart PCT application No. PCT/EP2016/054963, dated Jun. 13, 2016.
Huan Du et al., "A Virtual Keyboard Based on True-3D Optical Ranging", Published in: CH.
Wang Y et al., "Electrochemical delamination of CVD-grown graphene film: Toward the recyclable use of copper catalyst", XP002716759, ISSN: 1936-0851, DOI: 10.1021/NN203700W, "ACS NANO", dated Dec. 24, 2011, pp. 9927-9933, vol. 5, No. 12, Publisher: American Chemical Society, Published in: US.
Jian Zhang et al., "Electron Beam Lithography on Irregular Surfaces Using an Evaporated Resist", DOI: 10.1021/nn4064659, "ACS NANO", dated Mar. 26, 2014, pp. 3483-3489, vol. 8, No. 4, Publisher: American Chemical Society, Published in: CA.
Jiyoung Chang et al. , "Facile electron-beam lithography technique for irregular and fragile substrates", doi: http://dx.doi.org/10.1063/1.4900505, "Applied Physics Letters", dated Oct. 1, 2014, vol. 105, No. 17.
Zheng Han et al., "Homogeneous Optical and Electronic Properties of Graphene Due to the Suppression of Multilayer Patches During CVD on Copper Foils", dated 2013, DOI: 10.1002/adfm. 201301732, "Advanced Functional Materials", pp. 1-7, Publisher: WILEY-VCH Verlag GmbH & Co. KGaA, Weinheim.

Van Khrapach et al., Novel Highly Conductive and Transparent Graphene-Based Conductors, dated 2012, DOI: 10.1002/adma. 201200489, "Advanced Materials", pp. 2844-2849, vol. 24, Publisher: WILEY-VCH Verlag GmbH & Co. KGaA, Weinheim.
Xianrong Xing et al., "Electrochemical sensor based on molecularly imprinted film at polypyrrole-sulfonated graphene/hyaluronic acid-multiwalled carbon nanotubes modified electrode for determination of tryptamine", XP028353761, ISSN: 0956-5663, DOI: 10.1016/J. BIOS.2011.10.032, "Biosensors and Bioelectronics", dated Oct. 18, 2011, pp. 277-283, vol. 31, No. 1, Publisher: Elsevier BV, Published in: NL.
Stan Monstrey et al., "Assessment of burn depth and burn wound healing potential", DOI: http://dx/doi.prg/10.1016/j.burns.2008.01. 009, "BURNS", dated Sep. 1, 2008, pp. 761-769, vol. 34, No. 6, Publisher Elsevier Inc., Published in: BE.
Patricia Duran Ospina et al: "A Review in 6,7,13, Innovation in Ocular Prostheses and Visual 14 Implants: New Biomaterials and Neuro-Implants is the Challenge for the Visual Care", Journal of Ocular Diseases and Therapeutics, vol. 2, Jul. 3, 2014 (Jul. 3, 2014), pp. 9-16.
Office Action received for European Patent Application No. 15305351. 7, dated Sep. 21, 2015, 12 pages.
Luther C. Kloth, "Electrical StimulationTechnologies for Wound Healing", DOI: 10.1089/wound.2013.0459, "Advances in Wound Care", dated Mar. 8, 2013, pp. 81-90, vol. 3, No. 2, Publisher: Wound Healing Society.
L. C. Kloth: "Electrical Stimulation for Wound Healing: A Review of Evidence From In Vitro Studies, Animal Experiments, and Clinical Trials", The International Journal of Lower Extremity Wounds, vol. 4, No. 1, Mar. 1, 2005 (Mar. 1, 2005), pp. 23-44.
G. C. Zografos et al., "Laser Doppler Flowmetry in Evaluation of Cutaneous Wound Blood flow ujsing Various Suturing Techniques", "Ann. Surg ", dated Mar. 1992, pp. 266-268, vol. 215, No. 3, Published in: GB.
Authorized Officer: Cadamuro, Sergio, "International Search Report and Written Opinion" issued in PCT application No. PCT/EP2016/ 054964, dated May 10, 2016.
Applicant Initiated Interview Summary (PTOL-413) dated Sep. 29, 2020 for U.S. Appl. No. 15/556,984.
Ex Parte Quayle Action Mailed on Jul. 9, 2020 for U.S. Appl. No. 15/556,984.
Examiner Interview Summary Record (PTOL-413) dated Sep. 29, 2020 for U.S. Appl. No. 15/556,984.
Notice of Allowance and Fees Due (PTOL-85) dated Nov. 3, 2020 for U.S. Appl. No. 15/556,984.
English Translation of Office Action issued in Chinese Patent Application No. 201680026580.9 dated Sep. 23, 2020.
Tenhaeff et al., Initiated and Oxidative Chemical Vapor Deposition of Polymeric Thin Films: iCVD and oCVD, Apr. 18, 2008.
Notice of Allowance and Fees Due (PTOL-85) dated Feb. 10, 2021 for U.S. Appl. No. 15/556,984.
Notice of Allowance dated May 19, 2021 for U.S. Appl. No. 15/556,984.
Clement Hebert et al., "Flexible Graphene Solution-Gated Field-Effect Transistors: Efficient Transducers for Micro-Electrocorticography", "Advanced Functional Materials", dated 2017, 15 pp., doi:10.1002/adfm.201703976.
Jonas D. Buron et al., "Graphene Conductance Uniformity Mapping", "Nano Letters", ACS Publications, Aug. 31, 2012, https:// doi.org/10.1021/nl301551a.
Jonas Due Buron et al., "Electrically continuous graphene from single crystal copper verified by terahertz conductance spectroscopy and micro four-point probe". "Nano Letters", ACS Publications, Oct. 15, 2014, 24 pp., https://doi.org/10.1021/nl5028167.
Maria Kim et al., "Direct transfer of wafer-scale graphene films", "2D Materials", IOP Publishing, Jun. 22, 2017, 9 pp,m 4 (2017) 035004, https:doi.org/10.1088/2053-1583/aa780d.
Mohammad Mahdi Tavakoli et al., "Synergistic Roll-to-Roll Transfer and Doping of CVC-Graphene Using Parylene for Ambient-Stable and Ultra-Lightweight Photovoltaics", "Advanced Functional Materials", dated 2020, 11 pp., DOI: 10.1002/adfm .202001924.

(56) References Cited

OTHER PUBLICATIONS

Pauline Ronseaux et al., "Highly flexible superconducting films with metal-decorated composite 2D materials", "Journal of Applied Physics", 126, 165301 (2019), published Oct. 22, 2019, 10 pp., https://doi.org/10.1063/1.152615.
Non-Final Office Action received for U.S. Appl. No. 15/556,984, dated Feb. 26, 2020, 13 pages.
Requirement for Restriction/Election received for U.S. Appl. No. 15/556,984, dated Oct. 9, 2019, 7 pages.

* cited by examiner

METHOD OF FORMING A GRAPHENE DEVICE USING POLYMER MATERIAL AS A SUPPORT FOR A GRAPHENE FILM

FIELD

The present disclosure relates to the field devices partially formed of graphene, and to a method of forming a graphene device.

BACKGROUND

Graphene is a substance composed of carbon atoms forming a crystal lattice one atom in thickness. Various applications have been proposed for graphene, including its use in radio-frequency transistors and for forming transparent highly conductive and flexible electrodes, such as for displays. It is of particular benefit in applications where high mobility conductors are desired. Most applications of graphene require a macroscale-sized graphene layer, comprising one or a few layers of carbon atoms, which is transferred onto a substrate of a material selected based on the particular application.

Graphene is generally formed using a chemical vapor deposition (CVD) process, wherein graphene is deposited over a base substrate such as a copper foil. However, a difficulty is that it is relatively difficult to remove the graphene layer from the base substrate without damaging or polluting the graphene layer and/or degrading its conductivity.

Furthermore, in some embodiments it would be desirable to provide a method of forming a three-dimensional (3D) graphene device.

There is thus a need in the art for an improved method of forming a graphene device, and to one or more graphene devices formed based on such a method.

SUMMARY

It is an aim of embodiments of the present disclosure to at least partially address one or more needs in the prior art.

According to one aspect, there is provided a method of forming a graphene device, the method comprising: forming a graphene film over a substrate; depositing, by gas phase deposition, a polymer material covering a surface of the graphene film; and removing the substrate from the graphene film, wherein the polymer material forms a support for the graphene film.

According to one embodiment, the polymer material comprises a polymer from the n-xylylene family.

According to one embodiment, the polymer material comprises parylene.

According to one embodiment, the polymer layer is deposited with a thickness of between 10 nm and 5 mm.

According to one embodiment, the graphene film is formed over a three-dimensional surface of the substrate.

According to one embodiment, removing the substrate from the graphene film is performed by a process of electrochemical delamination or using an acid etch.

According to one embodiment, the above method of forming a graphene device is used for forming a sensor device that is to be placed over a three-dimensional form, wherein the substrate on which the graphene film is formed comprises a mold having the shape of a three-dimensional form.

According to one embodiment, the mold is formed of a first material and at least one zone of a second material. During the formation of the graphene film, graphene selectively forms only on the at least one zone of the second material, and the polymer material is deposited over the graphene film and at least a portion of the first material.

According to one embodiment, the method further comprises performing a further gas phase deposition of the polymer material to encapsulate the graphene film, after removing the substrate from the graphene film.

According to one embodiment, the graphene film is deposited to form a conductive track. The conductive track has a meandering form in a detection zone.

According to one embodiment, the graphene film is deposited in the form of a first plate of graphene formed in a detection zone and connected to a first conductive track. In addition, the method further comprises forming a further graphene film covered by a further deposition of polymer material, wherein the further graphene film is deposited in the form of a second plate of graphene. The first and second graphene films are assembled such that the first and second graphene plates form a capacitive interface in the detection zone separated by a layer of the polymer material.

According to a further aspect, there is provided a sensor device comprising a graphene film covered on at least one side by a polymer material. The polymer material has a detection element formed of a graphene film on a portion of its inside surface. The polymer material contacts and supports the graphene film.

According to one embodiment, the detection element comprises a meandering conductive track formed in a detection zone. The detection element electrically connects a first conductive track to a second conductive track.

According to one embodiment, the detection element comprises first and second graphene plates at least partially overlapping each other. The first graphene plate is connected to a first conductive track, and the second graphene plate is connected to a second conductive track.

According to one embodiment, the graphene device further comprises a detection circuit coupled to the first and second conductive tracks.

BRIEF DESCRIPTION OF THE DRAWINGS

The foregoing and other features and advantages will become apparent from the following detailed description of embodiments, given by way of illustration and not limitation with reference to the accompanying drawings, in which.

For ease of illustration, the various figures are not drawn to scale.

DETAILED DESCRIPTION

Throughout the present description, the term "connected" is used to designate a direct electrical connection between two elements, whereas the term "coupled" is used to designate an electrical connection between two elements that may be direct, or may be via one or more other components such as resistors, capacitors or transistors. Furthermore, as used herein, the term "substantially" is used to designate a range of +/−10 percent of the value in question.

Figure 1:
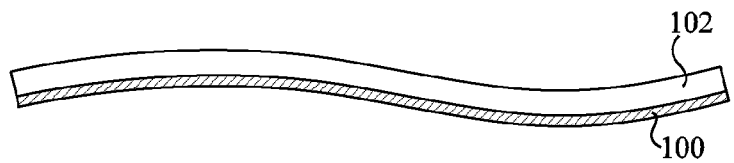
FIG. 1 is a cross-section view of a graphene device according to an example embodiment of the present disclosure.

FIG. 1 is a cross-section view of a graphene device comprising a film 100 of graphene, which is for example just one atom in thickness, or may have a thickness of up to 8 atom layers in some embodiments, depending on the application and the desired electrical conductivity. In particular, the graphene film 100 is for example formed of a plurality of graphene mono-layers attached together. In some embodiments, the graphene film 100 is doped in order to reduce its surface resistance, for example using P-dopants such as $AuCl_3$ and/or $HNO_3$. Additionally or alternatively, layers of one or more dopants such as $FeCl_3$ may be intercalated between one or more of the graphene layers to reduce the element resistance. For example, such a technique is described in more detail in the publication entitled "Novel Highly Conductive and Transparent Graphene-Based Conductors", I. Khrapach et al., Advanced Materials 2012, 24, 2844-2849, the contents of which is hereby incorporated by reference.

In plan view (not represented in FIG. 1), the graphene film 100 may have any shape, and for example has a surface area of anywhere between 1 $\mu m^2$ and 10 $cm^2$, depending on application.

The graphene film 100 is covered by a support 102 in the form of a layer of polymer material. The polymer material is for example selected from the family of n-xylylenes, and in one example comprises parylene. Parylene has the advantage of being capable of being stretch by up to 200% before breaking, and is capable of remaining flexible over a relatively wide temperature range. In one example, the polymer material comprises parylene C or parylene N. Both parylene C and parylene N have the advantage of being relative elastic, while parylene N has a slightly lower Young's modulus, and thus a higher elasticity, than parylene C.

As will be described in more detail below, the polymer support 102 has for example been formed by a gas phase deposition technique or by a spin deposition technique. The polymer support 102 for example has a thickness of between 10 nm and a few tens or hundreds of $\mu m$, or up to 5 mm, depending on the application. In some embodiments, the thickness of the polymer support 102 could be as low as 5 nm, and for example in the range 5 to 40 nm.

While in the example of FIG. 1 the polymer support is in the form of a layer having a substantially uniform thickness, as will become apparent from the embodiments described below, the polymer support could take other forms, depending on the particular application.

The combination of a graphene film 100 and a polymer support 102 provides a multi-layer that can have relatively high electrical conductance while remaining flexible and strong. Of course, while in the multi-layer of FIG. 1 there are just two layers—the graphene layer and the parylene layer that form a bi-layer, in alternative embodiments there could be one or more further layers. For example, the graphene layer could be sandwiched by parylene layers on each side, and/or one or more layers of further materials could be formed in contact with the graphene or parylene layer.

Furthermore, the use of a polymer such as parylene leads to a device that is biocompatible, making the device suitable for a variety of applications in which it can for example contact human or animal tissue.

Figure 2:
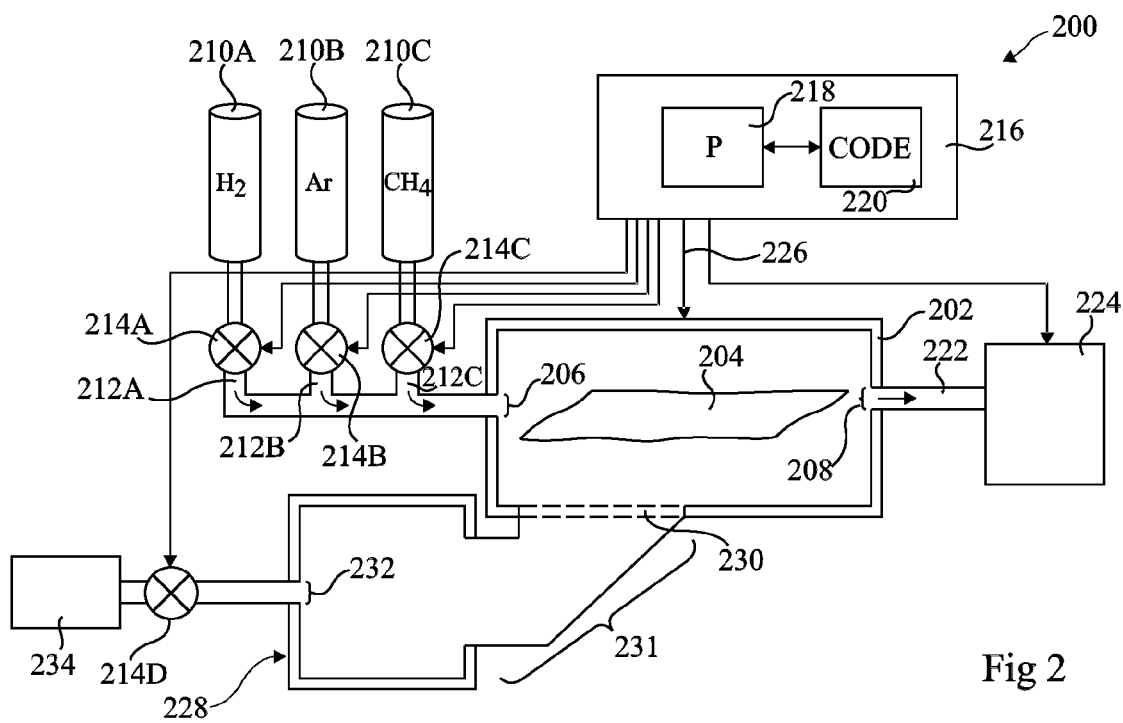
FIG. 2 schematically illustrates an apparatus for forming a graphene device according to an example embodiment of the present disclosure.

FIG. 2 illustrates apparatus 200 for forming a graphene device such as the device of FIG. 1 according to an example embodiment.

The step of forming the graphene film 100 for example involves forming mono-layers of graphene using the apparatus 200. A similar apparatus is described in the publication entitled "Homogeneous Optical and Electronic Properties of Graphene Due to the Suppression of Multilayer Patches During CVD on Copper Foils", Z. Han et al., Adv. Funct. Mater., 2013, DOI: 10.1002/adfm.201301732, the contents of which is hereby incorporated by reference.

The apparatus 200 comprises a reaction chamber 202 in which the graphene film is formed. For example, the reaction chamber 202 is a tube furnace or other type of chamber that can be heated.

A substrate 204, for example formed of a copper foil having a thickness of between 0.1 and 100 $\mu m$, is placed within the chamber 202. The substrate 204 provides a surface suitable for graphene formation. In particular, the material of the substrate 204 is for example selected as one that provides a catalyst for graphene formation, and for example has relatively low carbon solubility. For example, other possible materials for forming the substrate 204 include other metals such as nickel, cobalt, or ruthenium or copper alloys such as alloys of copper and nickel, copper and cobalt, copper and ruthenium, or dielectric materials, such as zirconium dioxide, hafnium oxide, boron nitride and aluminum oxide. In some embodiments, rather than being a foil, the substrate 204 could have a 3D form. The dimensions of such a substrate 204 could be anywhere from 0.1 $\mu m$ to several cm or more. Furthermore, the substrate 204 could be formed on a planar or 3D surface of a further substrate, for example of copper or another material such as sapphire.

An inlet 206 of the reaction chamber 202 allows gases to be introduced into the chamber, and an outlet 208 allows gases to be extracted from the chamber. The inlet 206 is for example supplied with gas by three gas reservoirs 210A, 210B and 210C, which in the example of FIG. 2 respectively store hydrogen ($H_2$), argon (Ar), and methane ($CH_4$). In alternative embodiments discussed in more detail below, different gases could be used. In particular, rather than hydrogen, a different etching gas, in other words one that is reactive with carbon, could be used, such as oxygen. Rather than argon, another inert gas could be used, such as helium. This gas is for example used to control the overall pressure in the reaction chamber 202, and could be omitted entirely in some embodiments. Rather than methane, a different organic compound gas could be used, such as butane, ethylene or acetylene.

The inlet 206 is coupled to: reservoir 210A via a tube 212A comprising a valve 214A; reservoir 210B via a tube 212B comprising a valve 214B; and reservoir 210C via a tube 212C comprising a valve 214C. The valves 214A to 214C control the flow rates of the respective gases into the chamber.

The valves 214A to 214C are for example electronically controlled by a computing device 216. The computing device 216 for example comprises a processing device 218, under the control of an instruction memory 220 storing program code for controlling at least part of the graphene formation process.

The outlet 208 is for example coupled via a tube 222 to an evacuation pump 224 for evacuating gases from the reaction chamber 202. The rate of evacuation by the pump 224 is for example also controlled by the computing device 216. As represented by an arrow 226, the computing device may also control one or more heating elements of the reaction chamber 202 to heat the interior of the chamber during the graphene formation process.

A method of forming a graphene film using the apparatus described above is for example discussed in more detail in the US patent application published as US2014/0326700, the contents of which are hereby incorporated by reference.

Furthermore, a deposition chamber 228 is for example provided for depositing the polymer layer over the graphene film. In the embodiment of FIG. 2, a trapdoor 230 in one wall of the chamber 202 and a passageway 231 between the chambers 202, 228 permit the substrate 204 with graphene film to be transferred between the chambers 202 and 228 without being exposed to the atmosphere. In alternative embodiments, the deposition chambers 202 and 228 could be separate from each other, and the substrate 204 with graphene film could be transferred without using a passageway.

The deposition chamber 228 for example comprises an inlet 232 coupled via a further valve 214D to a supply chamber 234 for providing a precursor for depositing the polymer material to cover the graphene film. The valve is for example controlled by the computing device 216. As mentioned above, the polymer material is for example deposited using gas phase deposition. The term "gas phase deposition" is considered here to include physical vapor deposition (PVD), chemical vapor deposition (CVD and atomic layer deposition (ALD). The precursor is for example heated in the supply chamber 234 to between 100° C. and 500° C. before being introduced as a vapor phase into the chamber 228 via the valve 214D.

Figure 3A:
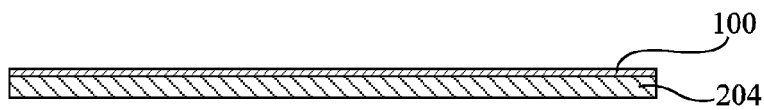
FIGS. 3A to 3C are cross-section views of the formation of a graphene device according to an embodiment of the present disclosure.
Figure 3B:
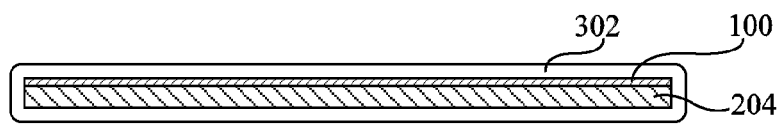
Figure 3C:
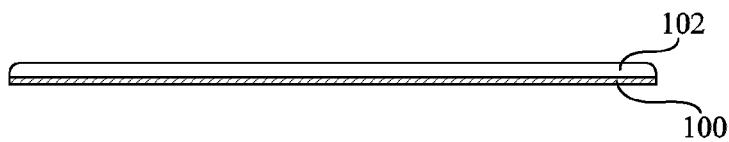

FIGS. 3A to 3C are cross-section views of a graphene device during its fabrication, for example using the apparatus of FIG. 2.

As shown in the FIG. 3A, initially it is assumed that a graphene film 100 has been formed by CVD over a substrate 204, which is for example a copper foil.

FIG. 3B illustrates an operation in which the polymer support is deposited covering the graphene film 100. In the example of FIG. 3B, the graphene is deposited over a relatively flat substrate 204, and the polymer material is deposited as a conformal layer 302 of substantially uniform thickness that encapsulates the device, including the substrate 204. For example, the device is suspended such that the polymer is deposited on all faces of the device. Alternatively, the device could be turned over during the deposition process. In yet further alternative embodiments, the polymer material could be deposited only over the graphene film 100. Furthermore, rather than being deposited in the form of a layer, the polymer material could be deposited in other forms, as will be described in more detail below.

FIG. 3C illustrates a subsequent operation in which the substrate 204 is removed, for example by an etching step or by delaminating the polymer layer with the graphene film 100 from the substrate 204. For example, the etching step involves removing the polymer coating covering the substrate 204, for example using a plasma etch, or by scraping with a sharp blade, in order to expose the surface of the substrate. The substrate is then removed, for example using a suitable etch, such as an acid etch or using an electrolysis technique. For example, an electrochemical delamination process may be performed as described in more detail in the publication entitled "Electrochemical delamination of CVD-Grown Graphene Film: Toward the Recyclable Use of Copper Catalyst", Yu Wang et al., the contents of which is hereby incorporated by reference to the extent permitted by the law.

This leaves the graphene film 100 with the polymer support 102. The present inventors have found that this polymer support 102 not only repairs to some extent any defects in the graphene film 100, but also limits further degradation of the graphene film 100 during the separation of the graphene film 100 from the substrate 204.

An advantage of the process described herein is that no transfer operation is required, reducing the risk that the properties of the graphene film will be degraded.

Indeed, graphene is generally formed using a chemical vapor deposition (CVD) process, wherein graphene is formed over a base substrate such as a copper foil. However, a difficulty is that it is relatively difficult to remove the graphene layer from the base substrate without damaging or polluting the graphene layer and/or degrading its conductivity.

By depositing a polymer material by gas phase deposition in contact with the graphene film, the polymer can remain attached to the graphene while the substrate is removed, for example by etching or by a delamination process, without a transfer step.

The process for forming a graphene device as described in relation to FIGS. 3A to 3C may be adapted to form a number of particular graphene devices as will now be described with reference to FIGS. 4 to 8.

Figure 4A:
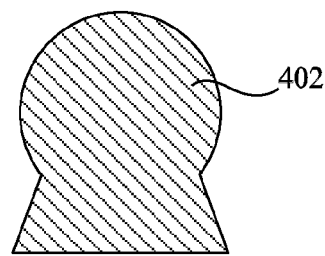
FIGS. 4A to 4C are cross-section views of the formation of a 3D graphene device according to an embodiment of the present disclosure.
Figure 4B:
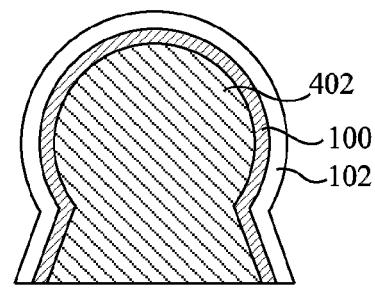
Figure 4C:
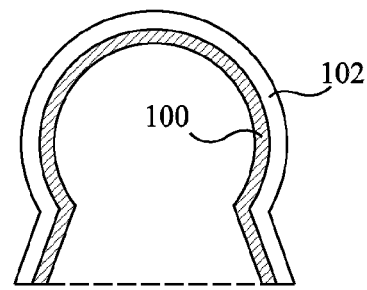

FIGS. 4A to 4C are cross-section views showing steps in a method of forming a graphene device comprising a three-dimensional graphene film according to an example embodiment. For example, such a device is suitable for being placed on or over a 3D form, such as a human or animal member, or a device or part of a device, and for example provides the function of a sensor, of a protection barrier, or the like.

FIG. 4A illustrates an example of a cross-section of a mold 402 over which the graphene device is to be formed. The 3D form of this mold 402 shown in FIG. 4A is merely one example used for illustration, and many different forms would be possible, depending on the particular application. The mold is formed of a material supporting graphene growth, such as copper.

FIG. 4B illustrates operations in which a graphene film 100 is formed over the mold 402, and a coating of polymer, such as of parylene, is then deposited over the graphene film 100.

FIG. 4C illustrates a subsequent operation in which the mold is removed, for example for example by an etching step or by delaminating the polymer layer with the graphene film 100 from the substrate 204, for example using a delaminating operation as described above.

Figure 5A:
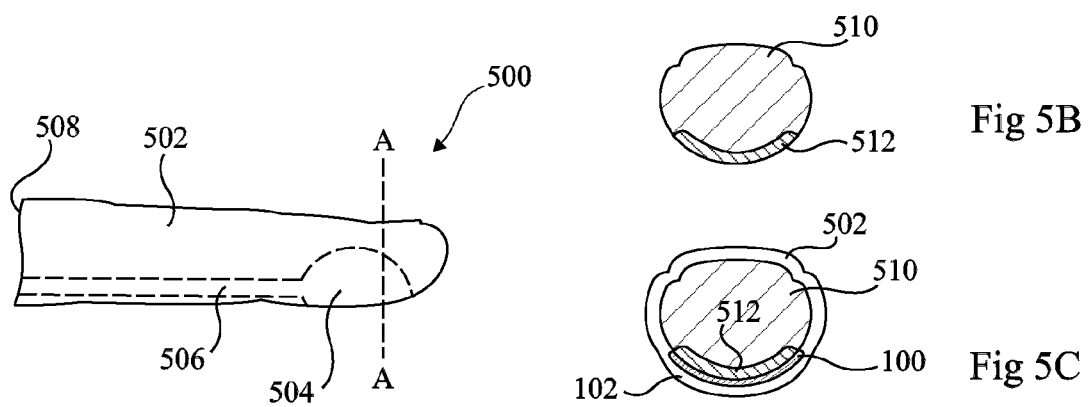
FIG. 5A illustrates a sensing device comprising graphene according to an example embodiment of the present disclosure.

FIG. 5A illustrates a sensing device 500, which in this example is designed to be worn by a user over their index finger or other body part. Of course, the technique that will be represented in relation to FIG. 5A could be applied a variety of different types of sensors having one or more sleeves or tubes adapted to fit around a body part of a human or animal. For example, the sensor could be in the form of a glove with a sensor in each finger of the glove in order to detect finger movements.

The sensor device 500 of FIG. 5A comprises a layer of a polymer such as parylene in the form of a sleeve or tube 502 that has dimensions closely fitting an index finger of a user. In the example of FIG. 5A, the sleeve 502 is closed at one end to form a finger. A film of graphene is formed on a portion of the inside surface of the sleeve 502, and provides an electrode 504 and conductive track 506. The electrode 504 is positioned to contact a portion of the underside of a finger near the tip of the finger. The electrode 504 is coupled via the conductive track 506 to an end 508 of the sleeve 502 opposite to the fingertip. While not shown in FIG. 5A, the end of the conductive track may be coupled via a wire to monitoring equipment, or a monitoring device could be implemented by an integrated circuit mounted on a side of the sleeve 502.

Figure 5B:
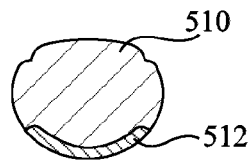
FIGS. 5B to 5D are cross-section views showing steps in a method of forming the sensing device of FIG. 5A according to an example embodiment.
Figure 5C:
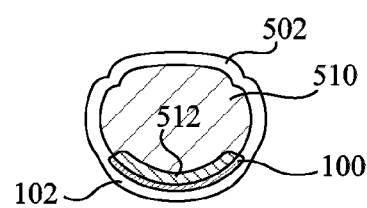
Figure 5D:
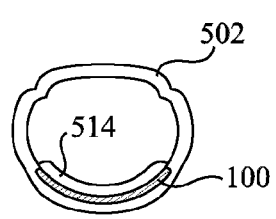

FIGS. 5B to 5D are cross-section views of the sensor device 500 of FIG. 5A during process steps for forming the sensor device of FIG. 5A. The cross-sections of FIG. 5B to 5D for example correspond to a line A-A shown in FIG. 5A, that passes through a portion of the sleeve 502 close to the fingertip and passing through the electrode 504.

As represented in FIG. 5B, a finger-shaped mold 510 of the same or approximately the same dimensions as the index finger to be used in the sensing device 500 is formed, for example of a material that does not support graphene growth, such as aluminum oxide. A thin plating 512 of a material such as copper, which supports graphene growth, is formed in the zone in which the electrode 504 and conductive track 506 are to be formed.

For example, in order to form the plated material 508 of copper or another material, one of two processes could be used.

A first process is for example described in more detail in the publication by J. Zhang et al. entitled "Electron Beam Lithography on Irregular Surfaces Using an Evaporated Resist", ACS Nana 2014, 8 (4), pp 3483-3489, the contents of which is hereby incorporated by reference to the extent permitted by the law. According to such a lithography process, an electron or photon sensitive resin is evaporated depending on the type of lithography to be used and on the desired resolution. Such a resin can be applied to non-planar surfaces in a desired pattern, followed by a lithography operation.

A second process is for example described in more detail in the publication by J. Chang et al. entitled "Facile electron-beam lithography technique for irregular and fragile substrates", Applied Physics Letters 105, 173109 (2014), the contents of which is hereby incorporated by reference to the extent permitted by the law. According to this technique, a resin film is prepared in advance by spin-coating and annealing. After this annealing, the resin film becomes solid and flexible, and can be transferred to the non-planar surface and follows it its 3D form. A lithography step can then be performed.

As represented in FIG. 5C, the mold is then for example placed in a CVD chamber such as the chamber 202 of the apparatus of FIG. 2, and a graphene film 100 is selectively formed over the plating 512. The polymer layer in the form of the sleeve 502 is then formed by coating a layer of polymer over the mold, including over the graphene film 100. The polymer coating for example has a thickness of between 50 and 500 µm. Where this polymer coating contacts the graphene film 100, it provides the polymer support for the graphene film 100.

As represented in FIG. 5D, polymer sleeve 502, and the graphene film 100, are for example removed from the mold, for example by a delamination process or electrochemical delamination process as described above.

While in the example of FIG. 5A the sensing device 500 comprises a single graphene conductive track 506 leading to a graphene plate forming the electrode 504, many other arrangements would be possible, as will now be described with reference to FIG. 6.

Figure 6:
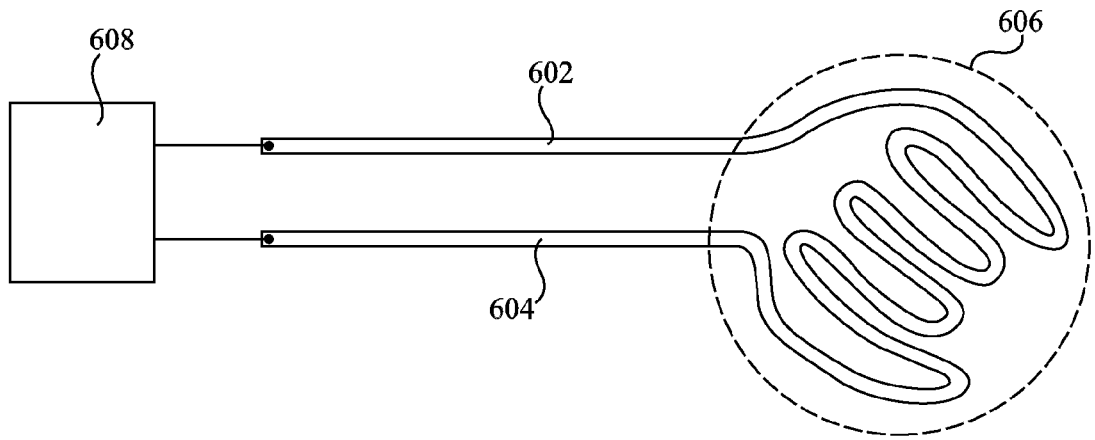
FIG. 6 illustrates a sensing element of the sensing device of FIG. 5A in more detail according to an example embodiment.

FIG. 6 illustrates the form of a graphene film 100 of the sensing device 500 of FIG. 5A according to one example in which two conductive tracks 602, 604 are provided leading to the electrode, and the electrode is implemented in the form of a meandering track electrically connecting the track 602 to the track 604 and formed with a detection zone 606. The tracks 602, 604 and the meandering track are for example formed using the lithography or spin-coating process described above with relation to FIG. 5B.

The conductive tracks 602, 604 are for example coupled to a detection circuit 608 for detecting a change in resistance of the conductive track formed in the detection zone. For example, the circuit 608 is adapted to apply a substantially constant current through the conductive tracks 602, 604 and to monitor the voltage drop between the conductive tracks 602, 604. Pressure applied to the graphene film in the zone 606 for example causes a change in the resistance of the graphene film by deforming the graphene film and/or causing a short circuit between sections of the meandering conductive track. Such a change in the resistance brings about a corresponding change in the voltage across the conductive tracks, which is detection by the detection circuit 608.

In one embodiment, the sensing device of FIG. 6 is used in a key stroke detection system, as will now be described in more detail with reference to FIG. 7.

Figure 7:
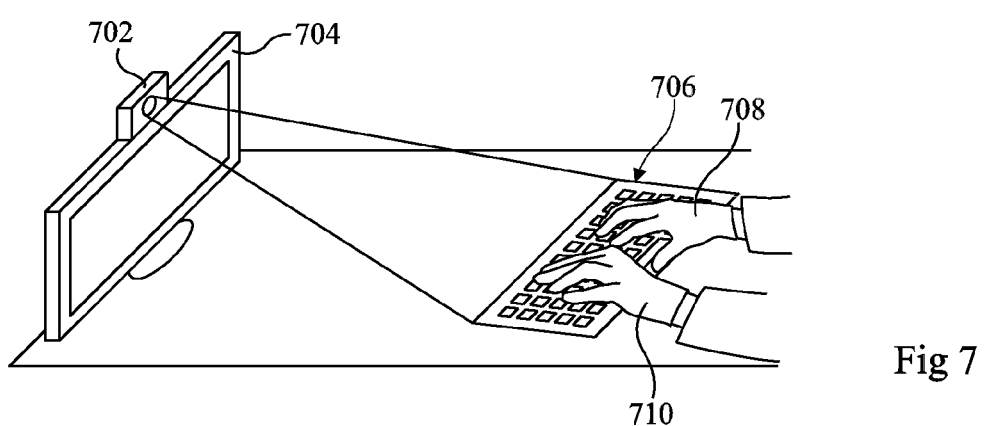
FIG. 7 illustrates a virtual keyboard arrangement according to an example embodiment.

FIG. 7 illustrates a virtual keyboard system in which a projector 702 is provided, in this example mounted on top of a display 704. The projector 702 projects an image 706 of a user interface onto a surface. In the example of FIG. 7, the user interface is a keyboard, but in alternative embodiments, other types of user interface can be projected. For example, the screen image could be projected in order to provide the functionality of a touch-screen. In such a case, the display 704 could be omitted.

The system also for example comprises a 3D ranging camera for detecting typing events made by a user on the projected image of the keyboard. Such a virtual keyboard system is for example discussed in the publication by Huan Du et al., entitled "A Virtual Keyboard Based on True-3D Optical Ranging", Proceedings of the British Machine Vision Conference, vol. 1, p. 220-229, the contents of which is hereby incorporated by reference to the extent permitted by the law.

A difficulty in such a virtual keyboard system is to confirm a typing event that has been detected visually. For example, a user may move a finger towards a key position with the intention of making a typing stroke, but then pull-back just short of touching the key position. Such a non-completed key stroke may be interpreted as an actual key stroke if based on visual data alone.

To deal with this problem, the user for example has one or more sensing devices similar to the ones of FIGS. 5 and 6 attached to one or more fingers. For example, the user wears gloves 708, 710 on their right and left hands respectively, comprising such a sensing device in one, several or all of its fingers.

While the meandering graphene track of FIG. 6 provides one possible means of detecting an exerted pressure in the detection zone 606, other techniques may be employed, as will now be described with reference to FIGS. 8A and 8B.

Figure 8A:
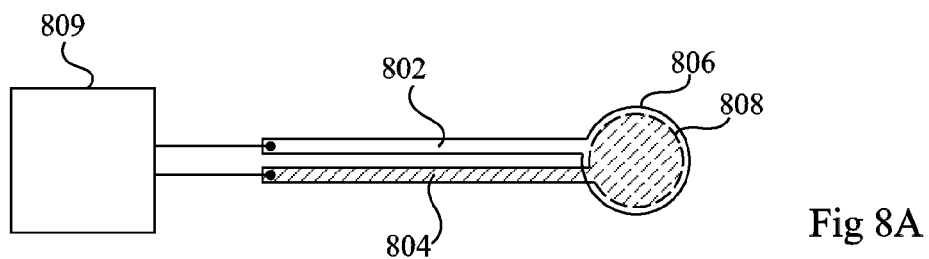
FIG. 8A illustrates in plan view a sensing element of the sensing device of FIG. 5A in more detail according to an alternative embodiment.

FIG. 8A is a plan view of a sensing apparatus comprising a pair of graphene films, respectively comprising conductive track 802 and 804. The conductive track 802 is connected at one end to a graphene plate 806, while the conductive track 804 is connected at one end to a graphene plate 808. The graphene plates 806, 808 are arranged such that they overlap, and they are separated by a deformable insulating layer (not illustrated in FIG. 8A) such that they have an associated capacitance. An external compressive force applied to the plates 806, 808, for example caused by a finger hitting a surface, will thus change the distance between the plates and cause a change in their capacitance, which can be detected by a detection circuit 809 coupled to the conductive tracks 802, 804.

Figure 8B:
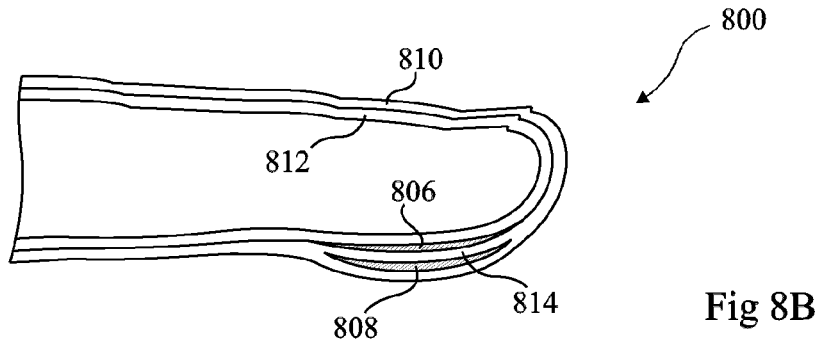
FIG. 8B is a cross-section view of the sensing device of FIG. 5A comprising the sensing element of FIG. 8A according to an example embodiment of the present disclosure.

FIG. 8B is a cross-section view of a sensing device 800 similar to the device 500 of FIG. 5A, but adapted to comprise the sensing apparatus of FIG. 8A.

The device 800 for example comprises an outer polymer sleeve 810, having formed therein the plate 808 and the conductive track 804 (not illustrated in FIG. 8B) running along the length of the sleeve. Such a structure is for example formed by the process described with reference to FIGS. 5B to 5D. The device 800 also for example comprises an inner polymer sleeve 812, having formed, on an outer surface thereof, the graphene plate 806, positioned adjacent to the graphene plate 808, and the conductive track 802 (not illustrated in FIG. 8B). This structure may also be formed by the method of FIGS. 5B to 5D, and by then turning the finger inside-out such that the graphene plate 806 is on the outside of the inner polymer sleeve 812. The polymer sleeve 812 is then positioned as an inner lining of the polymer sleeve 810 to achieve the structure of FIG. 8B. The graphene plates 806, 808 are separated by an insulating layer 814 for example formed of polymer, and which may comprise a polymer coating formed over the graphene plate 806 and/or a polymer coating formed over the graphene plate 808.

In use, the sensing device 800 is placed over a finger or other body part. A charge is then for example stored on one of the plates 806, 808 by applying a voltage between the conductive tracks 802, 804, for example by the detection circuit 809. The graphene plates 806, 808 then form a detection zone such that if pressure is applied in this zone, the capacitance of the plates 806, 808 will change, causing a change in the voltage on the conductive tracks 802, 804. This voltage change can be detected by the detection circuit 809.

An advantage of the graphene device described herein is that the polymer layer supports the graphene film 100, helping to maintain relative high conductive properties of the graphene film 100 as it is removed from the mold.

Furthermore, by depositing the polymer layer using gas phase deposition, the electrical conducting properties and mechanical properties of the graphene film can be particularly well conserved as the mold is removed. Indeed, gas phase deposition allows a thin polymer coating of relatively uniform thickness to be applied that has high conformity with the roughness of the surface of the graphene film, by closely following the contours of the graphene film. In view of its high conformity and uniformity, such a polymer layer exerts a lower stress on the graphene layer than would be possible with other deposition techniques such as spin coating.

Furthermore, gas phase deposition allows a supporting polymer layer to be realized that strictly conforms to a 3-dimensional shape of the graphene film, both at the nanoscale and at the microscale, respectively helping to preserve the integrity of the film by matching the wrinkles and thereby providing good electrical conductivity and helping to maintain the global 3D shape of the graphene film after the mold removal, allowing depositions on complex shapes such as gloves, etc.

An advantage of the sensing device described herein is that the polymer coating provides a support layer that remains flexible while holding a graphene electrode in a suitable position for detecting an event such as a key stroke.

Having thus described at least one illustrative embodiment, various alterations, modifications and improvements will readily occur to those skilled in the art.

For example, it will be apparent to those skilled in the art that while various devices comprising graphene have been described above and represented in the figures, there are many alternative applications of the method of forming the graphene and polymer multi-layer as described herein.

Furthermore, the various features described in relation to the various embodiments could be combined, in alterative embodiments, in any combination.

Such alterations, modifications, and improvements are intended to be within the scope of the invention. Accordingly, the foregoing description is by way of example only and is not intended as limiting. The invention is limited only as defined in the following claims and the equivalents thereto.

The invention claimed is:

1. A method of forming a conductive graphene device, the method comprising:
   forming a conductive graphene film over a substrate, the conductive graphene film consisting essentially of one to eight monolayers of carbon atoms, the conductive graphene film having a first surface and a second surface, the first surface covering the substrate;
   gas phase depositing a graphene support layer of parylene over the second surface of the conductive graphene film, the graphene support layer of parylene supporting the conductive graphene film during the operation of the conductive graphene device;
   removing the substrate from the conductive graphene film, thereby exposing the first surface of the conductive graphene film;
   wherein the graphene support layer of parylene is deposited with a thickness of between 5 nm and 5 mm;
   wherein the surface on which the conductive graphene film is formed comprises a mold having a shape of a three-dimensional form; and
   wherein:
      the mold is formed of a first material and at least one zone of a second material;
      during the formation of the conductive graphene film, graphene selectively forms on the at least one zone of the second material and not on the first material; and
      the graphene support layer of parylene is deposited over the conductive graphene film and at least a portion of the first material.

2. The method of claim 1, further comprising, after removing the substrate from the conductive graphene film, performing a further gas phase deposition of parylene to encapsulate the conductive graphene film.

3. A method of forming a conductive graphene device, the method comprising:

forming a conductive graphene film over a substrate, the conductive graphene film consisting essentially of one to eight monolayers of carbon atoms, the conductive graphene film having a first surface and a second surface, the first surface covering the substrate;

gas phase depositing a graphene support layer of parylene over the second surface of the conductive graphene film, the graphene support layer of parylene supporting the conductive graphene film during the operation of the conductive graphene device;

removing the substrate from the conductive graphene film, thereby exposing the first surface of the conductive graphene film;

wherein the graphene support layer of parylene is deposited with a thickness of between 5 nm and 5 mm; and wherein the conductive graphene film is deposited to form a conductive track having a meandering form in a detection zone.

4. A method of forming a conductive graphene device, the method comprising:

forming a conductive graphene film over a substrate, the conductive graphene film consisting essentially of one to eight monolayers of carbon atoms, the conductive graphene film having a first surface and a second surface, the first surface covering the substrate;

gas phase depositing a graphene support layer of parylene over the second surface of the conductive graphene film, the graphene support layer of parylene supporting the conductive graphene film during the operation of the conductive graphene device;

removing the substrate from the conductive graphene film, thereby exposing the first surface of the conductive graphene film;

wherein the graphene support layer of parylene is deposited with a thickness of between 5 nm and 5 mm; and wherein the conductive graphene film is deposited in the form of a first plate of graphene formed in a detection zone and connected to a first conductive track, and wherein the method further comprises:

forming a further conductive graphene film covered by a further deposition of the parylene, wherein the further conductive graphene film is deposited in the form of a second plate of graphene; and assembling the first and second conductive graphene films such that the first and second graphene plates form a capacitive interface in the detection zone separated by a layer of the parylene.

\* \* \* \* \*